United States Patent
Suyama

(10) Patent No.: US 8,873,713 B2
(45) Date of Patent: Oct. 28, 2014

(54) RADIATION DETECTING DEVICE

(75) Inventor: Toshiyasu Suyama, Hamamatsu (JP)

(73) Assignee: Hamamatsu Photonics K.K., Hamamatsu-shi, Shizuoka (JP)

(*) Notice: Subject to any disclaimer, the term of this patent is extended or adjusted under 35 U.S.C. 154(b) by 421 days.

(21) Appl. No.: 13/391,726

(22) PCT Filed: Jun. 29, 2010

(86) PCT No.: PCT/JP2010/061019
§ 371 (c)(1),
(2), (4) Date: Feb. 22, 2012

(87) PCT Pub. No.: WO2011/033838
PCT Pub. Date: Mar. 24, 2011

(65) Prior Publication Data
US 2012/0148024 A1    Jun. 14, 2012

(30) Foreign Application Priority Data
Sep. 18, 2009 (JP) ................. 2009-217544

(51) Int. Cl.
*H05G 1/64* (2006.01)
*H05G 1/62* (2006.01)
*H05G 1/60* (2006.01)
*H05G 1/38* (2006.01)
*H01L 27/146* (2006.01)
*G01N 23/04* (2006.01)
*G01V 5/00* (2006.01)

(52) U.S. Cl.
CPC ............... *G01N 23/04* (2013.01); *G01V 5/005* (2013.01)
USPC ................. 378/98.11; 378/98.9; 378/98.12; 250/370.09

(58) Field of Classification Search
USPC .................. 378/19, 62, 91, 98.8, 98.9, 98.11, 378/98.12, 204, 210, 901; 250/370.01, 250/370.08, 370.09, 370.11, 371
See application file for complete search history.

(56) References Cited

U.S. PATENT DOCUMENTS

2002/0168046 A1  11/2002  Hansen
2007/0057208 A1   3/2007  Joss et al.

FOREIGN PATENT DOCUMENTS

| JP | 61-143038 | 6/1986 |
|---|---|---|
| JP | 4-2907 | 1/1992 |
| JP | 5-68674 | 9/1993 |
| JP | 7-72257 | 3/1995 |
| JP | 2002-365368 | 12/2002 |

(Continued)

OTHER PUBLICATIONS

Machine Translation of JP 2009-85627.

*Primary Examiner* — Anastasia Midkiff
(74) *Attorney, Agent, or Firm* — Drinker Biddle & Reath LLP

(57) ABSTRACT

A radiation detection device 80 according to an embodiment is a radiation detection device for a foreign substance inspection using a subtraction method, including a first radiation detector 32 and a second radiation detector 42 that detect radiation transmitted through a specimen S, a timing control section 50 that controls detection timings, and an image correction section 34, wherein a first pixel width Wb1 in an orthogonal direction orthogonal to an image detection direction of each pixel of the first radiation detector 32 is smaller than a second pixel width Wb2 in the orthogonal direction of each pixel of the second radiation detector 42, the timing control section 50 synchronizes detection timings of the second radiation detector 42 to detection timings of the first radiation detector 32, and the image correction section 34 sums Wb2/Wb1 pixel data successive in an image from the first radiation detector 32.

4 Claims, 15 Drawing Sheets

(56) References Cited

FOREIGN PATENT DOCUMENTS

| | | |
|---|---|---|
| JP | 2006-502386 | 1/2006 |
| JP | 2008-538966 | 11/2008 |
| JP | 2009-82250 | 4/2009 |
| JP | 2009-85627 | 4/2009 |
| JP | 2009-85844 | 4/2009 |
| JP | 2009-85845 | 4/2009 |
| JP | 2009-094902 | 4/2009 |
| JP | 2010-117170 | 5/2010 |
| JP | 2010-117172 | 5/2010 |
| JP | 2010-190830 | 9/2010 |
| JP | 2011-064643 | 3/2011 |
| TW | 200801571 | 1/2008 |
| TW | 200842393 | 11/2008 |

Fig.7

|  | (a) | (b) |
|---|---|---|
| FIRST LINE | A | A + NOISE |
| SECOND LINE | B | B+A |
| THIRD LINE | C | C+B |
| FOURTH LINE | D | D+C |
| FIFTH LINE | E | E+D |
| SIXTH LINE | F | F+E |
| SEVENTH LINE | G | G+F |
| EIGHTH LINE | NOISE | NOISE + G |

Fig.12
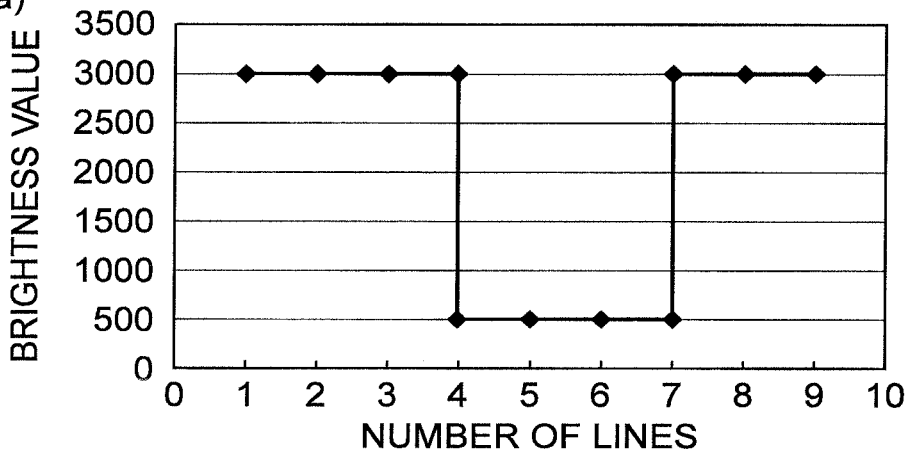
(a)
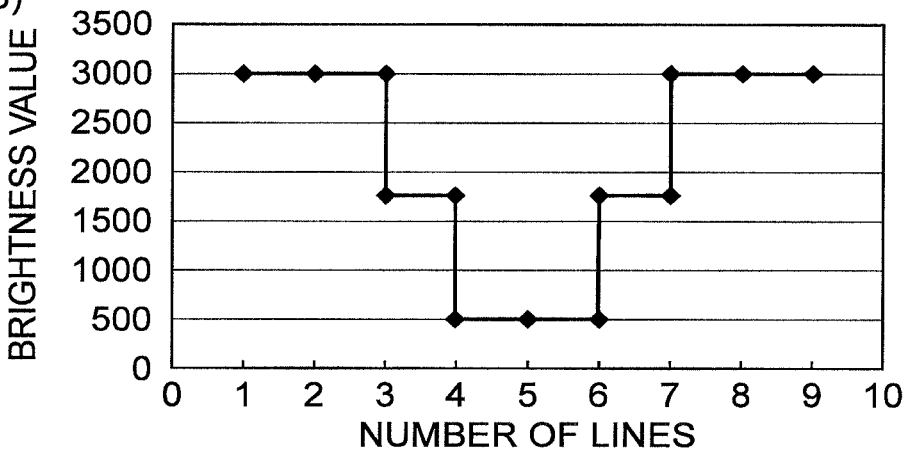
(b)
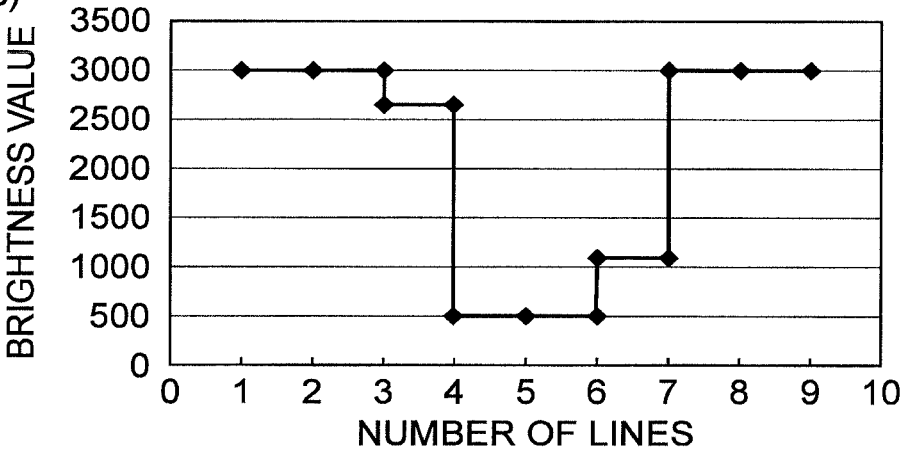
(c)

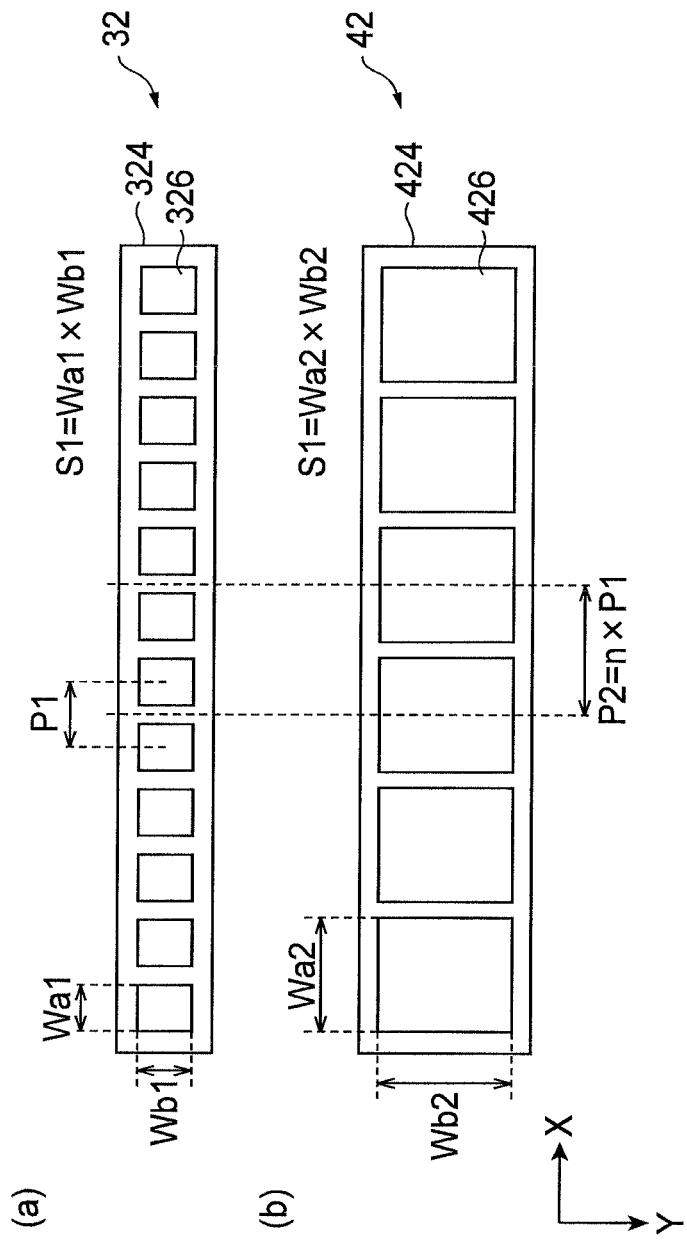

RADIATION DETECTING DEVICE

The present invention relates to a dual-energy radiation detection device.

BACKGROUND ART

Radiation detection devices that detect foreign substances, measure a component distribution, and measure weights, etc., in an in-line non-destructive inspection of a specimen that is conveyed by a belt conveyor or the like have been known. A radiation detection device includes a radiation detector having a scintillator layer and pixels, and detects radiation transmitted through a specimen and generates a radiation image.

This kind of radiation detection device is disclosed in Patent Literature 1. The radiation detection device described in Patent Literature 1 includes two radiation detectors with different pixel areas arranged side by side in a conveying direction of a belt conveyor. In this radiation detection device, large foreign substances are detected by the radiation detector with a larger pixel area, and small foreign substances are detected by the radiation detector with a smaller pixel area. By thus selecting a pixel size in advance according to a size of a foreign substance that a user desires to detect, foreign substance inspection accuracy can be improved.

As another method for improving the foreign substance inspection accuracy, a dual-energy radiation detection device has been known. A dual-energy radiation detection device includes two radiation detectors with different energy sensitivities, and detects radiation in a low-energy range (first energy range) and radiation in a high-energy range (second energy range) transmitted through a specimen. With this radiation detection device, a radiation image in a low-energy range and a radiation image in a high-energy range are simultaneously acquired, an image to which weighted subtraction and superimposition (for example, subtraction) is applied is created based on the radiation images, and according to a contrast difference in this image, a foreign substance is made to stand out, whereby realizing a foreign substance inspection with high accuracy.

CITATION LIST

Patent Literature

[Patent Literature 1] Japanese Patent Application Laid-Open No. 2009-85627

SUMMARY OF INVENTION

Technical Problem

For example, in an inspection of foreign substances in foods, it is required to carry out an inspection to detect bone, cartilage, and metal, etc., in meat as a foreign substance, and by utilizing the difference in radiation absorption between meat and a foreign substance (bone, cartilage, and metal, etc.), based on a contrast difference in a subtraction image of radiation images transmitted through these, a foreign substance is made to stand out, and accordingly, it is determined whether a foreign substance is present.

Here, bone and metal differ greatly in radiotransparency from (lower than) that of meat, so that a contrast difference in at least a radiation image acquired with one of the radiation detectors is great. As a result, a contrast difference in a subtraction image of the two radiation images is great, so that a foreign substance inspection can be easily carried out. However, cartilage, like meat, has high radiotransparency, and a difference in radiotransparency between these is small, so that the contrast differences in radiation images acquired with the radiation detectors become small. As a result, a contrast difference in a subtraction image of these radiation images also becomes small, so that the foreign substance inspection was difficult.

In this regard, as a result of intensive study, the inventors of the present invention found that a contrast difference in a radiation image between lightweight atoms of meat and cartilage, etc., that is, between substances both having high radiotransparency could be made larger in a radiation image in a lower energy range. Further, the inventors of the present invention found that, when a charge amount to be converted by each pixel was reduced by reducing the areas of pixels in the radiation detector for low-energy range detection, a charge amount difference in a radiation image between substances both having high radiotransparency could be made relatively large, and a contrast difference in a radiation image of these could be increased.

However, to reduce the areas of the pixels in the low energy radiation detector, if the pixel width in the direction orthogonal to the pixel array direction (image detection direction) is made smaller and the number of pixels (the number of line outputs) increases, the number of pixels (the number of line outputs) to be output from the low energy radiation detector and the number of pixels (the number of line outputs) to be output from the high energy radiation detector become different from each other, and as a result, it becomes difficult to carry out subtraction processing, that is, difference processing.

Therefore, an object of the present invention is to provide a radiation detection device that can easily carry out arithmetic processing based on radiation images acquired with two radiation detectors even when the radiation detectors have a different number of pixels.

Solution to Problem

A radiation detection device according to the present invention is a radiation detection device for a foreign substance inspection using a subtraction method, which detects radiation in a first energy range and radiation in a second energy range higher than the radiation in the first energy range that are transmitted through a specimen and incident from a radiation incident direction, comprising: a first radiation detector that is positioned on the upstream side with respect to the radiation incident direction, and detects radiation in the first energy range and generates an image corresponding to an image of the radiation; a second radiation detector that is positioned on the downstream side with respect to the radiation incident direction, and detects radiation in the second energy range and generates an image corresponding to an image of the radiation; a timing control section that controls detection timings of the first radiation detector and detection timings of the second radiation detector; and an image correction section that corrects an image from the first radiation detector. The first radiation detector includes a first pixel section that has a plurality of pixels arrayed along an image detection direction and acquires a first image based on an image of radiation in the first energy range, and the second radiation detector includes a second pixel section that has a plurality of pixels arrayed along the image detection direction and acquires a second image based on an image of radiation in the second energy range. A first pixel width Wb1 in an orthogonal direction orthogonal to the image detection direction of each of the plurality of pixels in the first pixel section is smaller than a second pixel width Wb2 in the orthogonal direction of each of the plurality of pixels in the second pixel section, the timing control section synchronizes detection timings of the second radiation detector to detection timings of the first radiation detector, and the image correction section sums Wb2/Wb1 pixel data successive in the image from the first radiation detector based on a ratio Wb2/Wb1 of the second pixel width Wb2 to the first pixel width Wb1.

When using a subtraction method, the two radiation detectors are required to image spatially and temporally the same position on a specimen. Therefore, with the type including two radiation detectors arranged side by side as described in Patent Literature 1, the detection timings of the radiation detectors must be adjusted. Even after the detection timings are adjusted, it is still difficult for the radiation detectors to image the same position, that is, exactly the same area in a specimen, so that position accuracy may become low. Thus, if a subtraction image in which the ends of the detection areas partially deviate from each other is created, pseudo edges such as a bright edge (white edge) and a dark edge (black edge) may be formed at an end portion of the detected object in the subtraction image.

On the other hand, in this radiation detection device, the first radiation detector and the second radiation detector are disposed so as to overlap in the radiation incident direction, that is, the radiation detection device is a vertically-piled type, so that the radiation detectors can easily image temporally the same position on a specimen without detection timing control simultaneously.

With this radiation detection device, detection timings of the second radiation detector are synchronized to detection timings of the first radiation detector by the timing control section so that at one detection timing, the second radiation detector acquires pixel data multiplied by the ratio Wb2/Wb1 of the second pixel width Wb2 to the first pixel width Wb1. Then, by the image correction section, based on the ratio Wb2/Wb1 of the second pixel width Wb2 to the first pixel width Wb1, Wb2/Wb1 pixel data successive in the image from the first radiation detector are summed, so that the corrected number of pixels of the image from the first radiation detector can be made equal to the number of pixels of the image from the second radiation detector. Therefore, even when the first pixel width in the orthogonal direction orthogonal to the image detection direction of the pixel in the first radiation detector is smaller than the second pixel width in the orthogonal direction of the pixel in the second radiation detector, that is, the number of pixels in the first radiation detector and the number of pixels in the second radiation detector are different from each other, arithmetic processing, for example, subtraction processing based on a radiation image acquired with the first radiation detector and a radiation image acquired with the second radiation detector can be easily carried out.

The above-described first radiation detector and the above-described second radiation detector are preferably arranged so that position deviations between detection positions on a specimen at detection timings of the first radiation detector and detection positions on the specimen at detection timings of the second radiation detector are not more than 0.3 times the first pixel width.

Due to an arrangement of the first radiation detector and the second radiation detector, a detection position on a specimen at a detection timing of the first radiation detector and a detection position on the specimen at a detection timing of the second radiation detector may greatly deviate from each other. Then, in a subtraction image based on a radiation image acquired with the first radiation detector and a radiation image acquired with the second radiation detector, a white edge and a black edge may appear before and after a portion corresponding to this detection position.

However, when the first radiation detector and the second radiation detector are arranged so that the position deviations between the detection positions on the specimen at the detection timings of the first radiation detector and the detection positions on the specimen at the detection timings of the second radiation detector become not more than 0.3 times the first pixel width, in a subtraction image based on a radiation image acquired with the first radiation detector and a radiation image acquired with the second radiation detector, a white edge and a black edge can be prevented from appearing before and after a portion corresponding to this detection position, and an excellent subtraction image can be obtained.

The above-described timing control section preferably delays either the detection timings of the first radiation detector or the detection timings of the second radiation detector.

Accordingly, a position deviation between a detection position on the specimen at a detection timing of the first radiation detector and a detection position on the specimen at a detection timing of the second radiation detector due to an arrangement of the first radiation detector and the second radiation detector can be reduced. Therefore, a white edge and a black edge can be prevented from appearing before and after a portion corresponding to this detection position in a subtraction image based on a radiation image acquired with the first radiation detector and a radiation image acquired with the second radiation detector, so that an excellent subtraction image can be obtained.

The first radiation detector described above includes a first scintillator layer that extends along the image detection direction and converts an image of radiation in the first energy range into an optical image, and a first pixel section that acquires a first image based on the optical image converted by the first scintillator layer, and the second radiation detector described above includes a second scintillator layer that extends along the image detection direction and converts an image of radiation in the second energy range into an optical image, and a second pixel section that acquires a second image based on the optical image converted by the second scintillator layer.

Advantageous Effects of Invention

According to the present invention, in a dual-energy radiation detection device using a subtraction method, even when the number of pixels of two radiation detectors are different from each other, arithmetic processing, for example, subtraction processing based on radiation images acquired with these radiation detectors can be easily carried out.

BRIEF DESCRIPTION OF DRAWINGS

FIG. 7 is a drawing showing pixel data of images output from the low energy detector and the high energy detector shown in FIG. 2.

FIG. 12 is a diagram showing brightness files of images when detecting the same specimen.

FIG. 15 is a drawing showing X-ray incidence planes of a low energy detector and a high energy detector in a dual-energy sensor according to an exemplary variation of the present invention.

DESCRIPTION OF EMBODIMENTS

Figure 1:
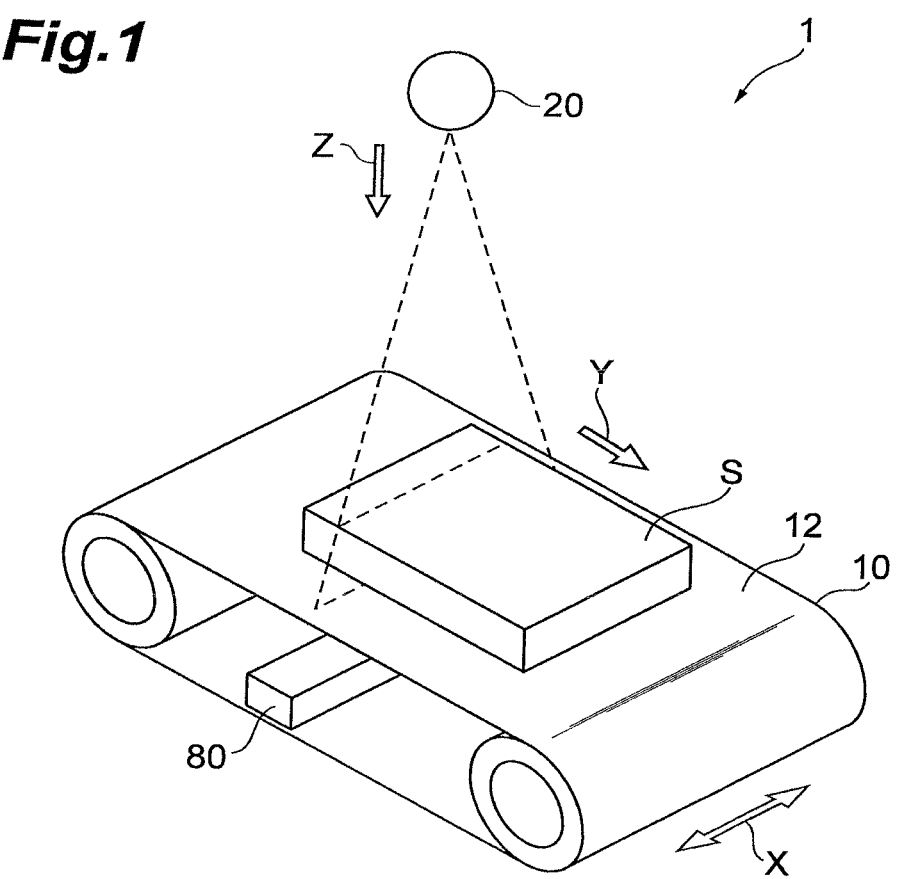
FIG. 1 is a perspective view of an X-ray foreign substance inspection device according to the present embodiment.

Hereinafter, a preferred embodiment of the present invention is described with reference to the drawings. In the drawings, portions identical to or equivalent to each other are designated by the same reference signs.

Figure 2:
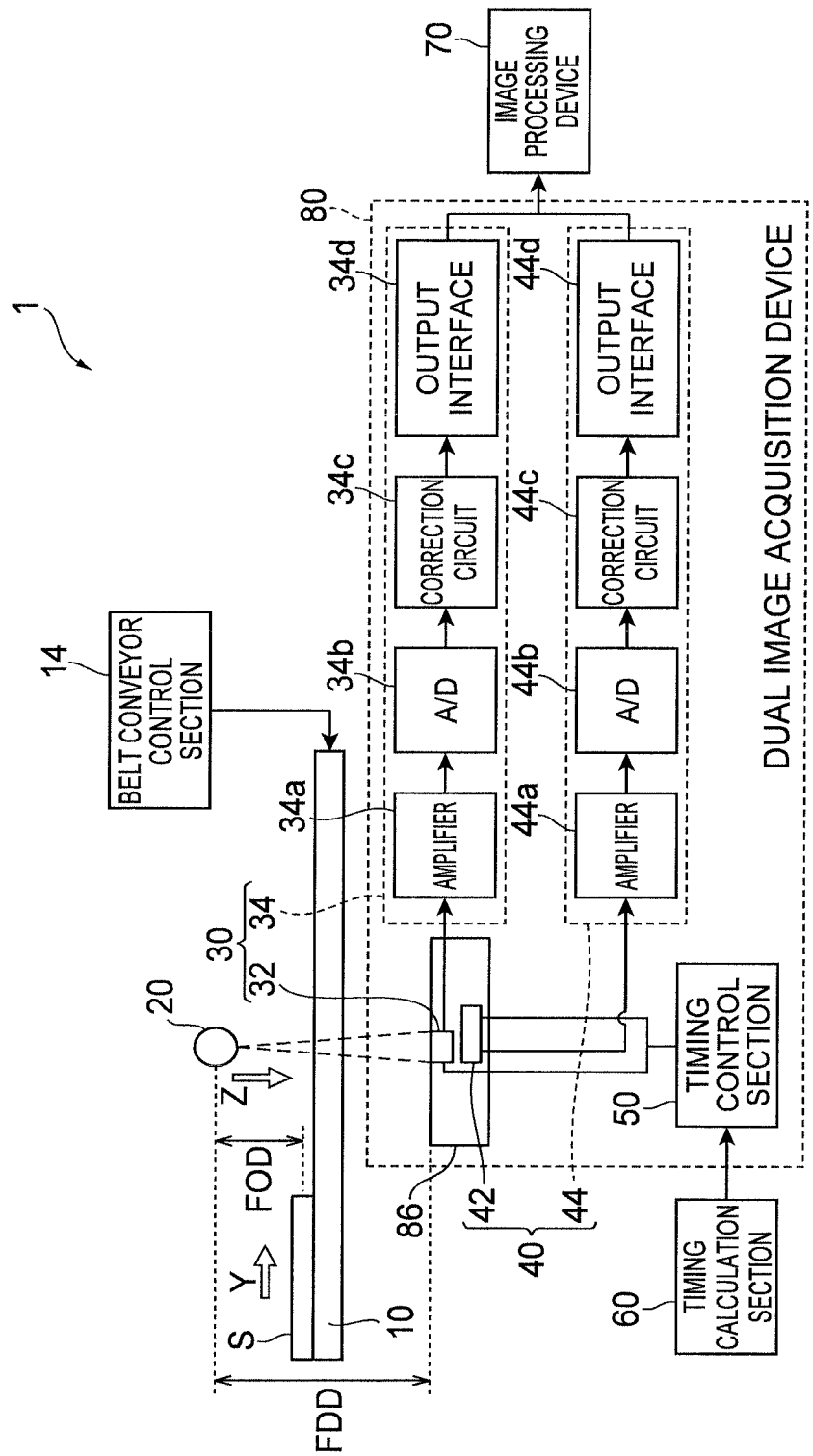
FIG. 2 is a schematic configuration view of the X-ray foreign substance inspection device according to the present embodiment.

FIG. 1 is a perspective view of an X-ray foreign substance inspection device according to the present embodiment, and FIG. 2 is a schematic configuration view of the X-ray foreign substance inspection device according to the present embodiment. As shown in FIG. 1 and FIG. 2, the X-ray foreign substance inspection device 1 irradiates X-rays (radiation) from an X-ray source onto a specimen S in an irradiation direction Z, and detects transmitted X-rays transmitted through the specimen S of the irradiated X-rays in a plurality of energy ranges. The X-ray foreign substance inspection device 1 carries out a foreign substance inspection and a baggage inspection, etc., to detect foreign substances included in a specimen S by using a transmitted X-ray image. Such an X-ray foreign substance inspection device 1 includes a belt conveyor 10, an X-ray irradiator 20, a low energy image acquisition section 30, a high energy image acquisition section 40, a timing control section 50, a timing calculation section 60, and an image processing device 70. The low energy image acquisition section 30, the high energy image acquisition section 40, and the timing control section 50 constitute a dual-energy radiation detection device 80 according to an embodiment of the present invention.

The belt conveyor 10 includes a belt portion 12 on which a specimen S is placed as shown in FIG. 1. The belt conveyor 10 conveys the specimen S in a conveying direction Y at a predetermined conveying speed by moving the belt portion 12 in the conveying direction Y. The conveying speed of the specimen S is, for example, 48 m/min. The belt conveyor 10 can change the conveying speed to, for example, 24 m/min and 96 m/min by the belt conveyor control section 14 as appropriate. The belt conveyor control section 14 can change the height position of the belt portion 12. By changing the height position of the belt portion 12, the distance between the X-ray irradiator 20 and the specimen S can be changed. By this change, the resolution of X-ray transmitted images to be acquired with the low energy image acquisition section 30 and the high energy image acquisition section 40 can be changed. The specimen S to be conveyed by the belt conveyor 10 is composed of various objects, for example, foods such as meat, rubber products such as tires, baggage and cargo to be subjected to baggage inspections and cargo inspections for security and safety, and other resin products and metal products, resource materials such as mineral substances, waste to be separated and collected (recycled) as resources, and electronic components, etc.

The X-ray irradiator 20 is an X-ray source that irradiates X-rays in the irradiation direction Z onto the specimen S. The X-ray irradiator 20 is a point light source, and diffuses and irradiates X-rays in a predetermined angle range in a detection direction X orthogonal to the irradiation direction Z and the conveying direction Y. The X-ray irradiator 20 is disposed above the belt portion 12 at a predetermined distance to the belt portion 12 so that the X-ray irradiation direction Z is directed toward the belt portion 12 and X-rays diffuse to the entirety in the width direction (detection direction X) of the specimen S. The X-ray irradiator 20 has an irradiation range set to a predetermined divided region in the longitudinal direction (conveying direction Y) of the specimen S, and by conveying the specimen S in the conveying direction Y by the belt conveyor 10, X-rays are irradiated onto the entirety in the longitudinal direction of the specimen S.

The low energy image acquisition section 30 includes a low energy detector (first radiation detector) 32 and a low energy image correction section (image correction section) 34.

The low energy detector 32 is positioned on the upstream side with respect to the X-ray incident direction Z, and detects X-rays in a low-energy range (first energy range) transmitted through the specimen S of the X-rays irradiated from the X-ray irradiator 20 and generates low energy image data (first radiation image data).

The low energy image correction section 34 is a section that amplifies and corrects low energy image data generated by the low energy detector 32. The low energy image correction section 34 includes an amplifier 34a that amplifies low energy image data, an A/D converter 34b that converts the low energy image data amplified by the amplifier 34a, a correction circuit 34c that applies predetermined correction processing to the low energy image data converted by the A/D converter 34b, and an output interface 34d that outputs the image data corrected by the correction circuit 34c to the outside. The details of the low energy image correction section (image correction section) 34 will be described later.

The high energy image acquisition section 40 includes a high energy detector (second radiation detector) 42 and a high energy image correction section 44.

The high energy detector 42 is positioned on the downstream side with respect to the X-ray incident direction Z, and detects X-rays in a high-energy range (second energy range) transmitted through the specimen S and the low energy detector 32 of the X-rays irradiated from the X-ray irradiator 20 and generates high energy image data (second radiation image data). The low-energy range detected by the low energy detector 32 and the high-energy range detected by the high energy detector 42 are not clearly discriminated from each other, but overlap to some extent.

The high energy image correction section 44 is a section that amplifies and corrects high energy image data generated by the high energy detector 42. The high energy image correction section 44 includes an amplifier 44a that amplifies high energy image data, an A/D converter 44b that A/D converts the high energy image data amplified by the amplifier 44a, a correction circuit 44c that applies predetermined correction processing to the high energy image data converted by the A/D converter 44b, and an output interface 44d that outputs the image data corrected by the correction circuit 44c to the outside.

The timing control section 50 controls transmitted X-ray detection timings in the low energy detector 32 and transmitted X-ray detection timings in the high energy detector 42. The timing control section 50 reduces an image deviation in the following subtraction processing according to detection timings calculated by the timing calculation section 60 so that low energy image data and high energy image data correspond to each other. The details of the timing control section 50 and the timing calculation section 60 will be described later.

The image processing device 70 is a device that generates a subtraction image as a synthesized image by carrying out arithmetic processing (subtraction processing) for calculating difference data between low energy image data detected and generated by the low energy detector 32 and high energy image data detected and generated by the high energy detector 42. The detection timings of both energy image data to be input into the image processing device 70 are controlled by the timing control section 50 so that both image data correspond to each other. The image processing device 70 outputs the subtraction image generated by the arithmetic processing to a display, etc., and displays it thereon. By this output display, foreign substances, etc., included in the specimen S can be visually confirmed. It is also possible that the subtraction image is not output and displayed but only data is output so that foreign substances, etc., included in the specimen S are directly detected from the image data by detection processing on the image data.

Figure 3:
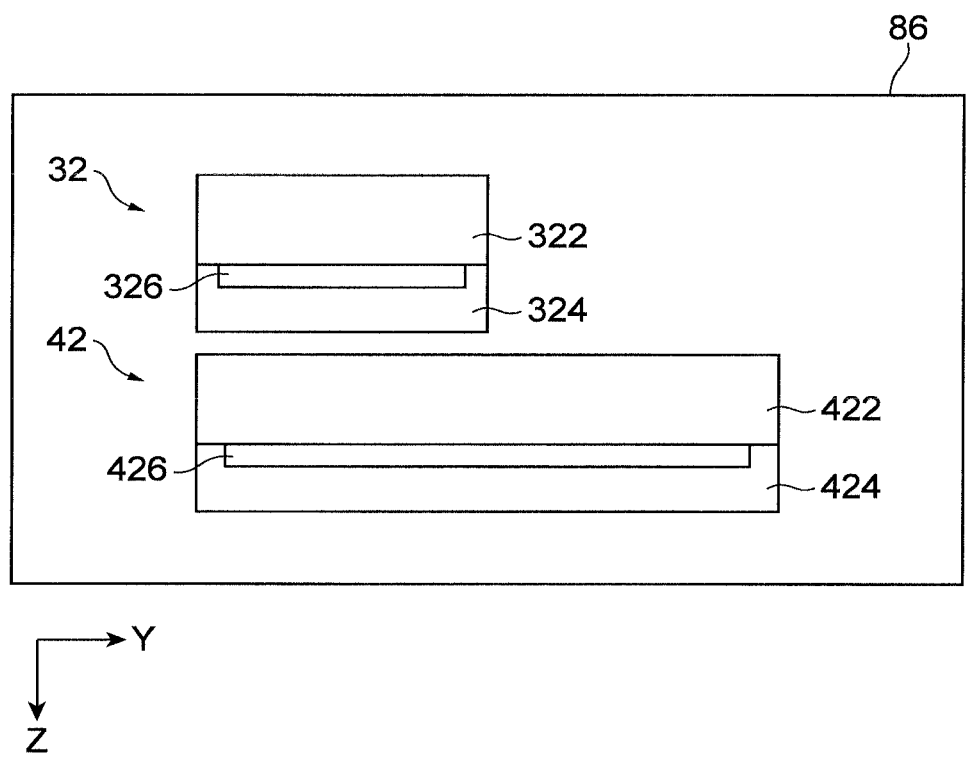
FIG. 3 is a schematic structural drawing of a dual-energy sensor in a radiation detection device according to an embodiment of the present invention.

Next, the low energy detector 32 and the high energy detector 42 are described in detail. FIG. 3 is a schematic structural drawing of a dual-energy sensor 86 consisting of the low energy detector 32 and the high energy detector 42 in the radiation detection device 80 shown in FIG. 2, and FIG. 4 is a drawing showing an X-ray incidence plane (a) of the low energy detector 32 and an X-ray incidence plane (b) of the high energy detector 42.

Figure 4:
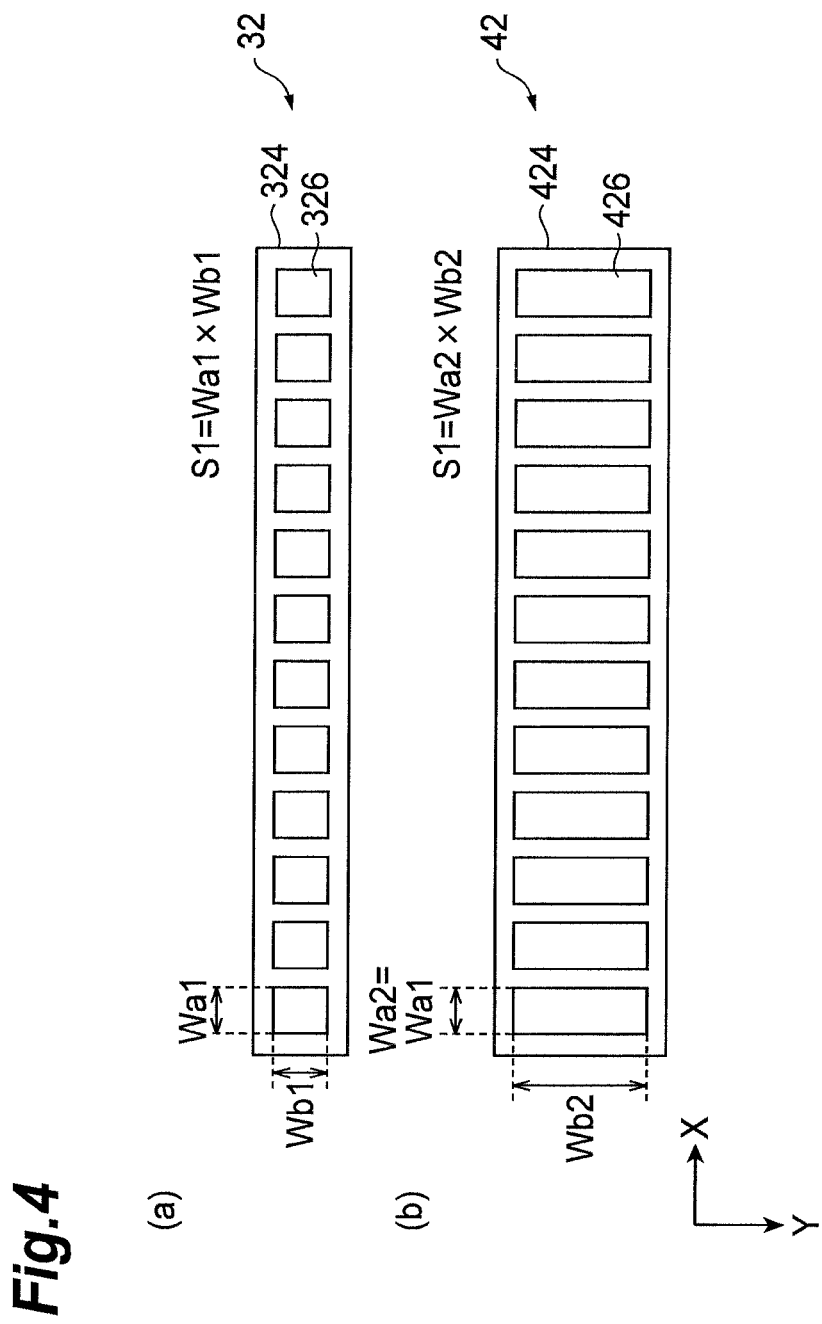
FIG. 4 is a drawing showing X-ray incidence planes of a low energy detector and a high energy detector in the dual-energy sensor shown in FIG. 3.

As shown in FIG. 3 and FIG. 4, the low energy detector 32 includes a low energy scintillator layer (first scintillator layer) 322 and a low energy line sensor (first pixel section) 324. The low energy scintillator layer 322 extends along the image detection direction X and converts an image of X-rays in the low-energy range into an optical image. The low energy line sensor 324 includes a plurality of pixels 326 arrayed along the image detection direction X, and acquires a low energy image (first image) based on the optical image converted by the low energy scintillator layer 322. Thus, the low energy detector 32 detects X-rays in the low-energy range.

Similarly, the high energy detector 42 includes a high energy scintillator layer (second scintillator layer) 422 and a high energy line sensor (second pixel section) 424. The high energy scintillator layer 422 extends along the image detection direction X and converts an image of X-rays in the high-energy range into an optical image. The high energy line sensor 424 includes a plurality of pixels 426 arrayed along the image detection direction X, and acquires a high energy image (second image) based on the optical image converted by the high energy scintillator layer 422. The high energy detector 42 thus detects X-rays in the high-energy range.

Here, the pixel width (first image detection direction width) Wa1 in the image detection direction X of each of the plurality of pixels 326 in the low energy line sensor 324 is equal to the pixel width (second image detection direction width) Wa2 in the image detection direction X of each of the plurality of pixels 426 in the high energy line sensor 424. On the other hand, the pixel width (first orthogonal direction width) Wb1 in an orthogonal direction (conveying direction Y) orthogonal to the image detection direction X of each of the plurality of pixels 326 in the low energy line sensor 324 is smaller than the pixel width (second orthogonal direction width) Wb2 in the orthogonal direction Y of each of the plurality of pixels 426 in the high energy line sensor 424. Thus, the area (first area) S1 of each of the plurality of pixels 326 in the low energy line sensor 324 is smaller than the area (second area) S2 of each of the plurality of pixels 426 in the high energy line sensor 424. Specifically, the number of pixels (the number of line outputs) in the low energy line sensor 324 is larger than the number of pixels (the number of line outputs) in the high energy line sensor 424.

The material of the low energy scintillator layer 322 and the material of the high energy scintillator layer 422 may be the same, or may be different from each other. For example, as materials of the low energy scintillator layer 322 and the high energy scintillator layer 422, Gd2O2S:Tb, CsI:Tl, CdWO4, CaWO4, GSO, LGSO, BGO, LSO, YSO, YAP, Y2O2S:Tb, YTaO4:Tm, etc., are applicable, and a combination of materials is selected according to X-rays to be detected. The low energy detector 32 and the high energy detector 42 may be X-ray detectors having an energy discrimination function using a direct conversion system of CdTe (cadmium telluride), etc.

Here, in a foreign substance inspection in foods, it is required to carry out the inspection to detect bone, cartilage, and metal, etc., in meat as a foreign substance, and by utilizing the difference in radiation absorption between meat and a foreign substance (bone, cartilage, and metal, etc.), a foreign substance is made to stand out due to contrast differences in a subtraction image of radiation images transmitted through these, and it is determined whether a foreign substance is present.

Here, bone and metal differ greatly in radiotransparency from (lower than) that of meat, so that a contrast difference in at least a radiation image acquired with one of the radiation detectors is great. As a result, a contrast difference in a subtraction image of two radiation images is great, so that a foreign substance inspection is easily carried out. However, cartilage, like meat, has high radiotransparency, and the difference in radiotransparency between these is small, so that contrast differences in radiation images acquired with both radiation detectors become small. As a result, a contrast difference in a subtraction image of these radiation images is also small, so that a foreign substance inspection was difficult.

However, in the low energy detector 32 that detects a radiation image in the low-energy range, which can make a contrast difference in a radiation image between lightweight atoms of meat and cartilage, etc., that is, between substances both having high radiotransparency comparatively large, when the pixel width Wb1 in the conveying direction Y of each pixel 326 is reduced, that is, the area S1 of each pixel 326 in the low energy detector 32 is made smaller, a charge amount to be converted by each pixel 326 becomes smaller, and a charge amount difference in a radiation image between lightweight atoms of meat and cartilage, etc., that is, between substances both having high radiotransparency, can be made relatively large, and a contrast difference in a radiation image of these can be made larger. As a result, a foreign substance inspection can be easily carried out.

Next, the correction circuit 34c in the low energy image correction section 34, the timing control section 50 and the timing calculation section 60 are described in detail.

Figure 5:
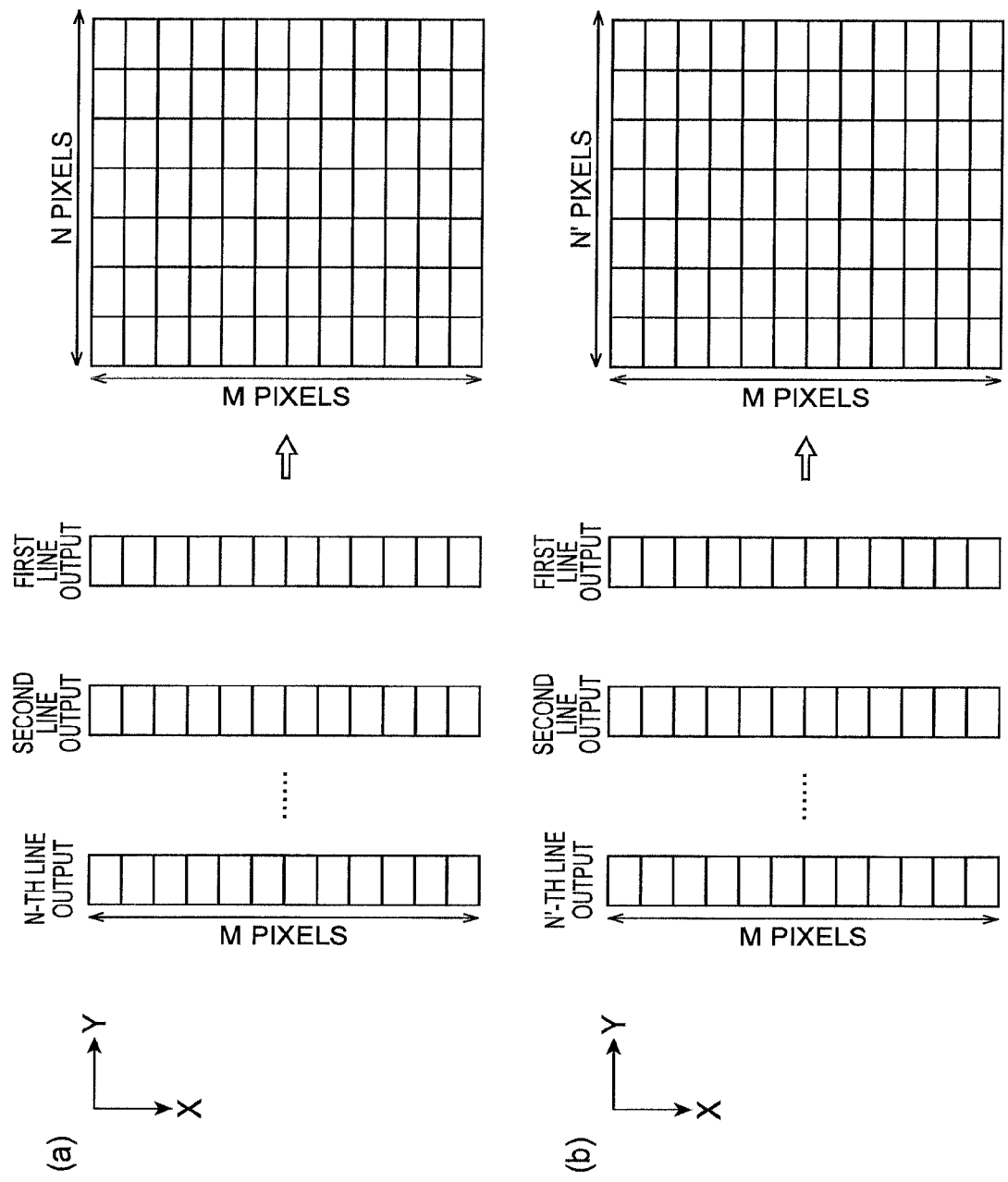
FIG. 5 is a conceptual diagram showing image processings in a low energy image correction section and a high energy image correction section shown in FIG. 2.

FIG. 5 is a conceptual diagram showing image processing (a) by the low energy image correction section 34 and image processing (b) by the high energy image correction section 44.

As shown in FIG. 5(a), the number of pixels of an image to be output from the low energy detector 32 becomes M×N as a result of two-dimensional image processing applied to M pixels (detection direction X)×N line outputs (conveying direction Y). On the other hand, referring to FIG. 5(b), the number of pixels of an image to be output from the high energy detector 42 becomes M×N' (N'<N) as a result of two-dimensional image processing applied to M pixels (detection direction X)×N' line outputs (conveying direction Y).

Thus, when the pixel area S1 of the low energy detector 32 and the pixel area S2 of the high energy detector 42 are different from each other, that is, when the pixel width Wb1 in the conveying direction Y of the low energy detector 32 and the pixel width Wb2 in the conveying direction Y of the high energy detector 42 are different from each other, the number of line outputs N of the image to be output from the low energy detector 32 and the number of line outputs N' of the image to be output from the high energy detector 42 are different from each other, that is, the number of pixels N in the conveying direction Y of the image from the low energy detector 32 and the number of pixels N' in the conveying direction Y of the image from the high energy detector 42 are different from each other, and therefore, it is difficult to create a subtraction image by carrying out different processing of these images.

Therefore, the timing control section 50 makes the number of line outputs N of the image to be output from the low energy detector 32 and the number of line outputs N' of the image to be output from the high energy detector 42 equal to each other by synchronizing the detection timings of the low energy detector 32 and the detection timings of the high energy detector 42 with each other. Specifically, the number of pixels N in the conveying direction Y of the image from the low energy detector 32 and the number of pixels N' in the conveying direction Y of the image from the high energy detector 42 are made equal to each other.

Figure 6:
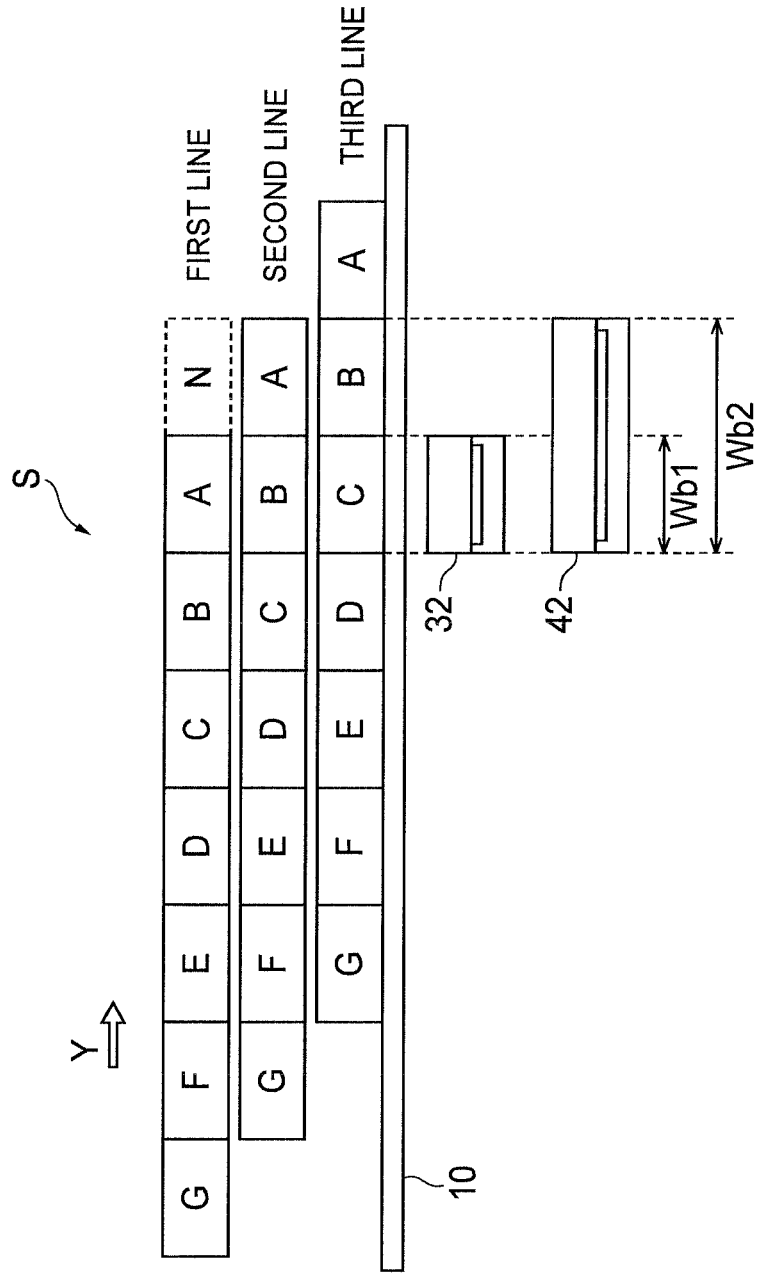
FIG. 6 is a conceptual diagram of detection timing control to be carried out by the timing control section shown in FIG. 2.

FIG. 6 is a conceptual diagram of detection timing control to be carried out by the timing control section 50, and FIG. 7 is a drawing showing pixel data (a) of the image to be output from the low energy detector 32 and pixel data (b) of the image to be output from the high energy detector 42.

For example, the timing control section 50 supplies repetitive pulse signals for detection timings to the low energy detector 32 and the high energy detector 42. The timing control section 50 synchronizes the detection timings with each other by synchronizing these repetitive pulse signals with each other. The repetitive pulse signals are controlled according to control signals from the timing calculation section 60 by using, for example, PLL (Phase Locked Loop: phase synchronization circuit), etc. In the timing calculation section 60, the values of the control signals, that is, the detection timings are adjusted by considering, for example, the conveying speed V of the belt conveyor 10, the pixel width Wb1 or Wb2 in the conveying direction Y of the pixels of the line sensor, the distance FOD from the light source 20 to the specimen S, and the distance FDD from the light source 20 to the detector 32 or 42, etc. Respective values are set by, for example, a user in advance.

In detail, the timing control section 50 controls the period of the repetitive pulse signal for the low energy detector 32 to the pixel width Wb1 in the conveying direction Y of the pixel 326 in the low energy detector 32, and synchronizes the period of the repetitive pulse signal for the high energy detector 42 with the period of the repetitive pulse signal for the low energy detector 32. Thus, in the present embodiment, the detection timings of the high energy detector 42 that has the larger pixel width in the conveying direction Y are adjusted not by the pixel width Wb2 of its own pixel 426 but by the pixel width Wb1 of the pixel 326 in the low energy detector 32.

Then, for example, as shown in FIG. 6 and FIG. 7, at a first line detection timing, pixel data A is detected by the low energy detector 32, and pixel data A+noise N can be detected by the high energy detector 42. Next, at a second line detection timing, pixel data B is detected by the low energy detector 32, and pixel data B+A can be detected by the high energy detector 42. Next, at a third line detection timing, pixel data C is detected by the low energy detector 32, and pixel data C+B can be detected by the high energy detector 42. Next, at a fourth line detection timing, pixel data D is detected by the low energy detector 32, and pixel data D+C can be detected by the high energy detector 42. Next, at a fifth line detection timing, pixel data E is detected by the low energy detector 32, and pixel data E+D can be detected by the high energy detector 42. Next, at a sixth line detection timing, pixel data F is detected by the low energy detector 32, and pixel data F+E can be detected by the high energy detector 42. Next, at a seventh line detection timing, pixel data G is detected by the low energy detector 32, and pixel data G+F can be detected by the high energy detector 42. Next, at an eighth line detection timing, noise N is detected by the low energy detector 32, and noise N+pixel data G can be detected by the high energy detector 42.

Then, for difference processing, correction processing is carried out to match pixel data of the low energy detector 32 side and pixel data of the high energy detector 42 side by the correction circuit 34c in the low energy image correction section 34. In detail, the correction circuit 34c in the low energy image correction section 34 sums Wb2/Wb1 pixel data successive in the image from the low energy detector 32 based on the ratio Wb2/Wb1 of the pixel width Wb2 of each pixel 426 in the high energy detector 42 to the pixel width Wb1 of each pixel 326 in the low energy detector 32.

Figure 8:
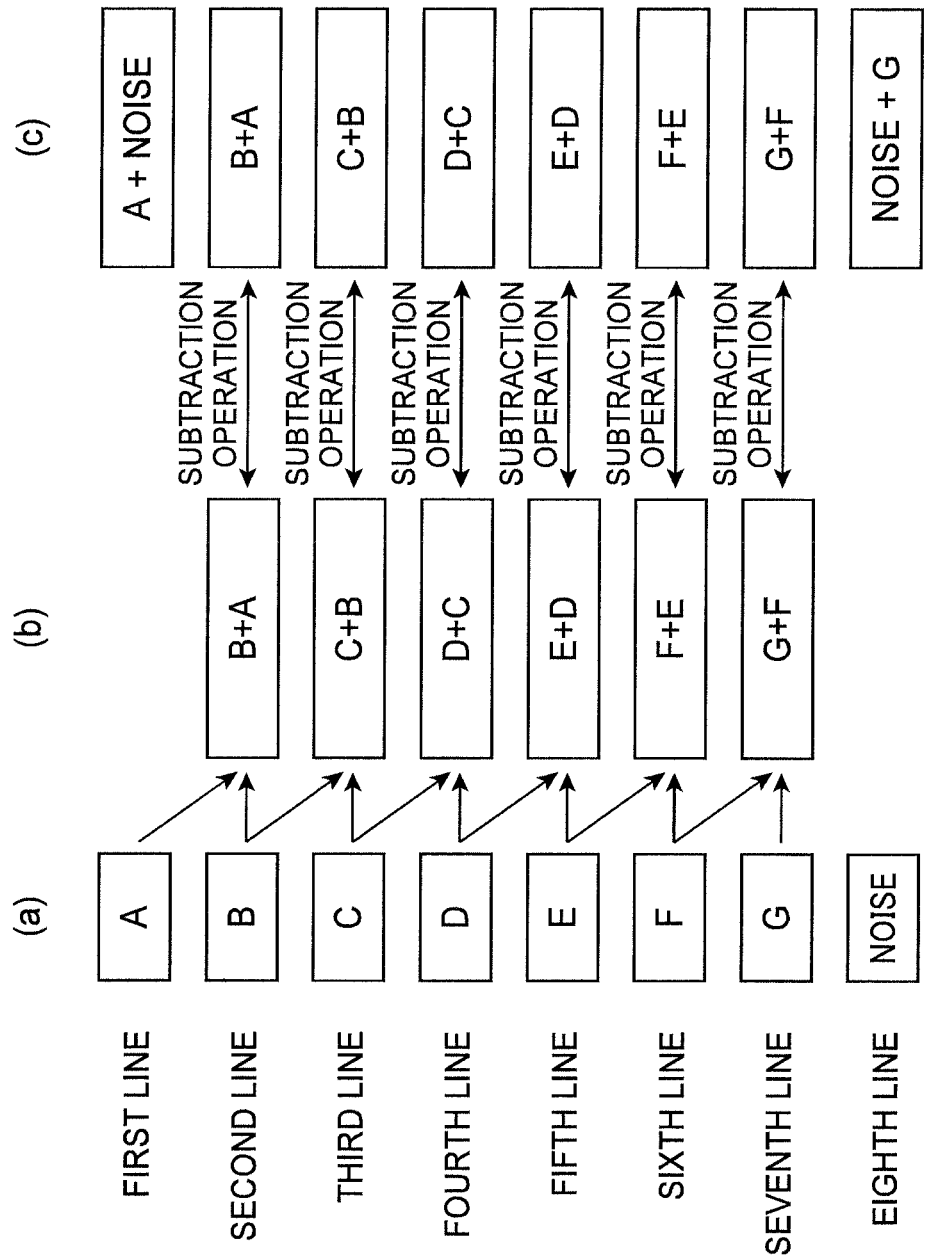
FIG. 8 is a conceptual diagram showing image correction processing to be carried out by the low energy image correction section shown in FIG. 2.

In the present embodiment, Wb2/Wb1=2, and therefore, as shown in FIG. 8, the correction circuit 34c generates correction data B+A by adding, to the pixel data B detected at the second line, pixel data A detected one line before, generates correction data C+B by adding, to the pixel data C detected at the third line, the pixel data B detected one line before, generates correction data D+C by adding, to pixel data D detected at the fourth line, the pixel data C detected one line before, generates correction data E+D by adding, to pixel data E detected at the fifth line, the pixel data D detected one line before, generates correction data F+E by adding, to pixel data F detected at the sixth line, the pixel data E detected one line before, and generates correction data G+F by adding, to pixel data G detected at the seventh line, the pixel data F detected one line before. Thus, the correction circuit 34c generates correction data B+A, C+B, D+C, E+D, F+E, and G+F corresponding to pixel data B+A, C+B, D+C, E+D, F+E, and G+F of the high energy detector 42 side, respectively.

Thus, with the radiation detection device 80 according to the present embodiment, the detection timings of the high energy detector 42 are synchronized to the detection timings of the low energy detector 32 by the timing control section 50, so that the high energy detector 42 acquires pixel data multiplied by the ratio Wb2/Wb1 of the pixel width Wb2 to the pixel width Wb1 in the conveying direction Y with respect to the low energy detector 32. Then, by the correction circuit 34c in the low energy image correction section 34, based on the ratio Wb2/Wb1 of the pixel width Wb2 to the pixel width Wb1, Wb2/Wb1 pixel data successive in the image from the low energy detector 32 are summed, so that the corrected number of pixels in the image from the low energy detector 32 and the number of pixels in the image from the high energy detector 42 can be made equal to each other. Therefore, even when the pixel width Wb1 in the conveying direction Y of the image in the low energy detector 32 is smaller than the pixel width Wb2 in the conveying direction Y in the high energy detector 42, that is, even when the number of pixels in the low energy detector 32 and the number of pixels in the high energy detector 42 are different from each other, arithmetic processing, for example, subtraction processing based on a radiation image acquired with the low energy detector 32 and a radiation image acquired with the high energy detector 42 can be easily carried out.

Figure 9:
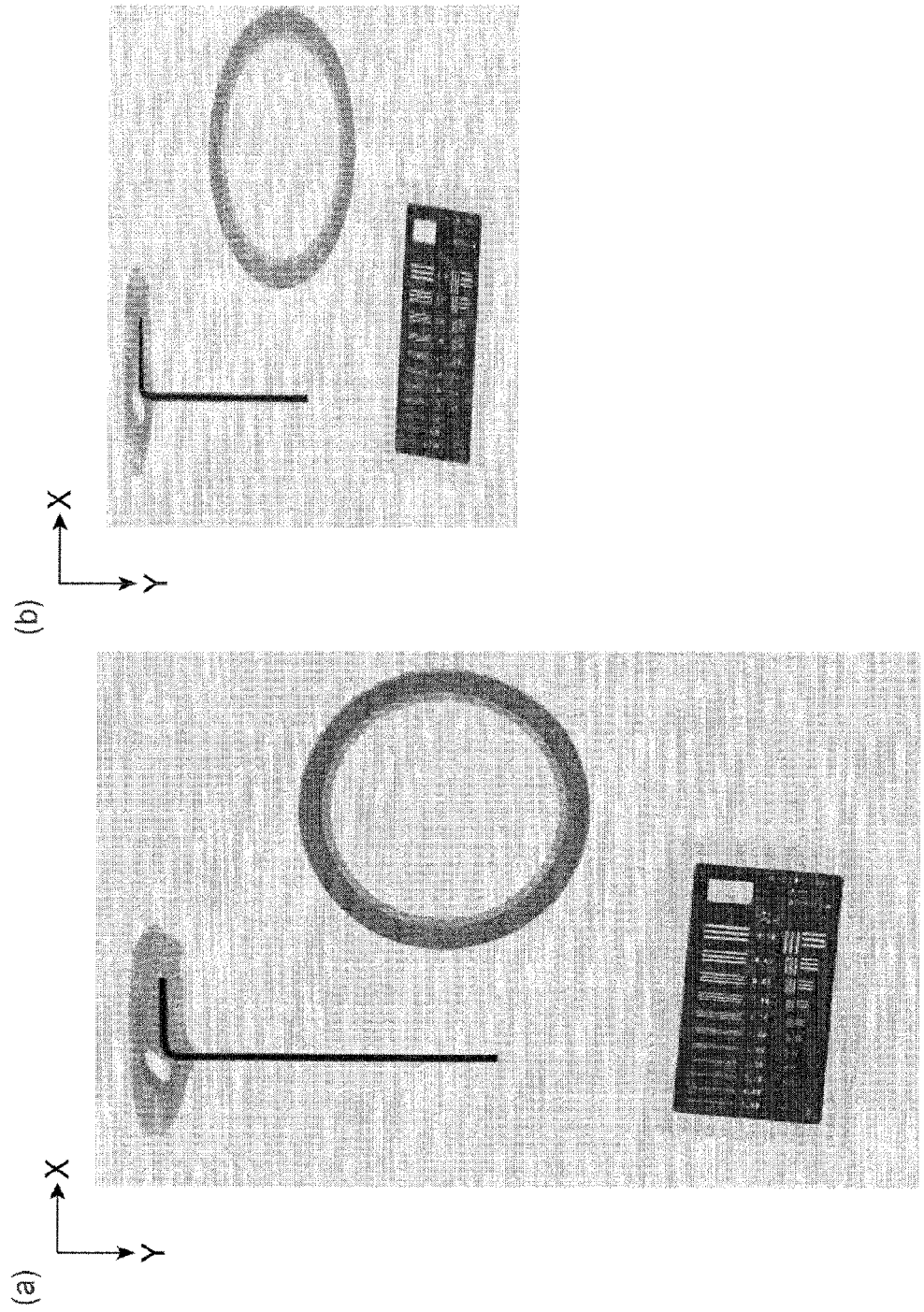
FIG. 9 is a view showing images detected by the low energy detector and the high energy detector when detection timing control and image correction processing according to the present embodiment are not carried out.
Figure 10:
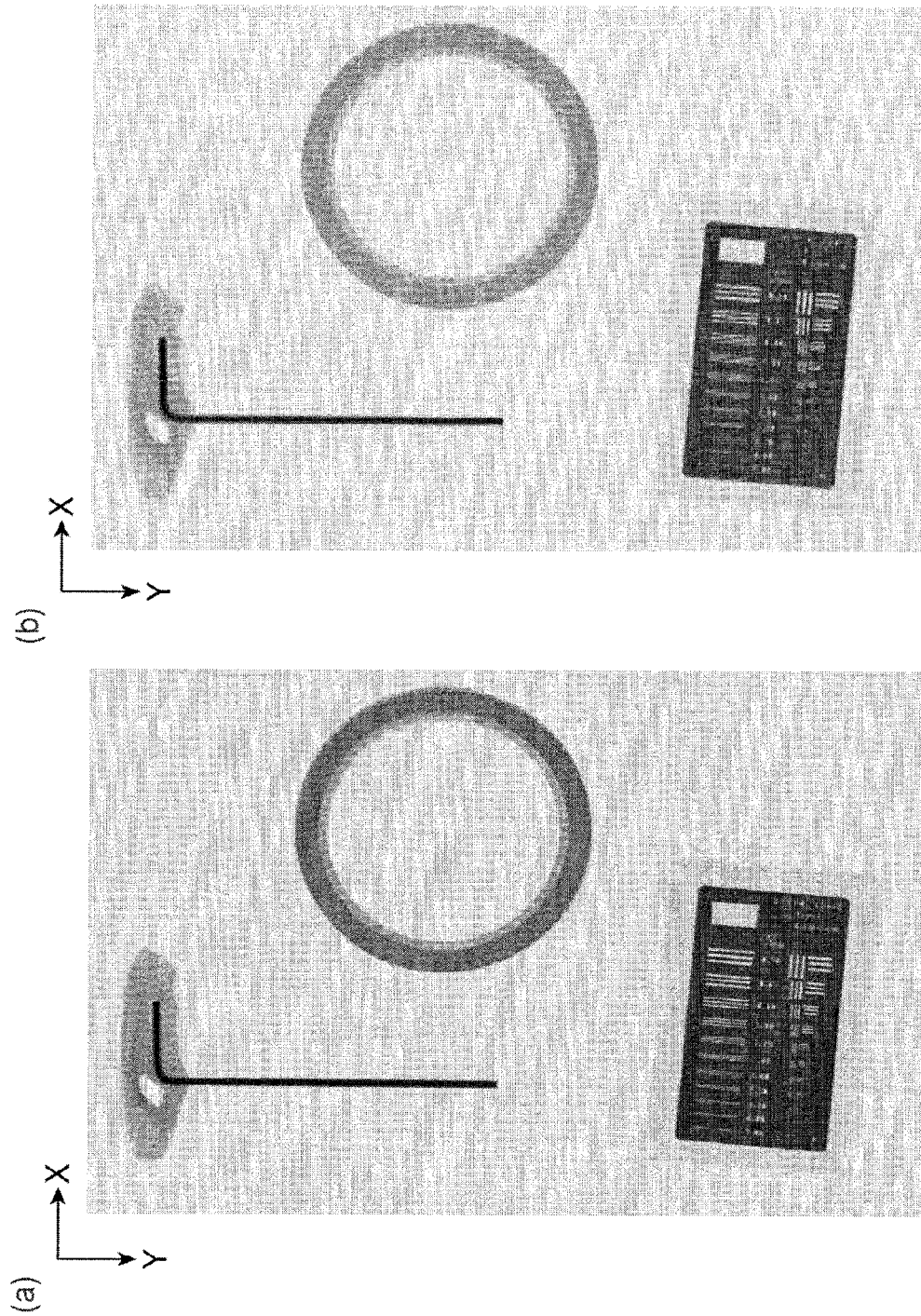
FIG. 10 is a view showing images detected by the low energy detector and the high energy detector when detection timing control and image correction processing according to the present embodiment are carried out.
Figure 11:
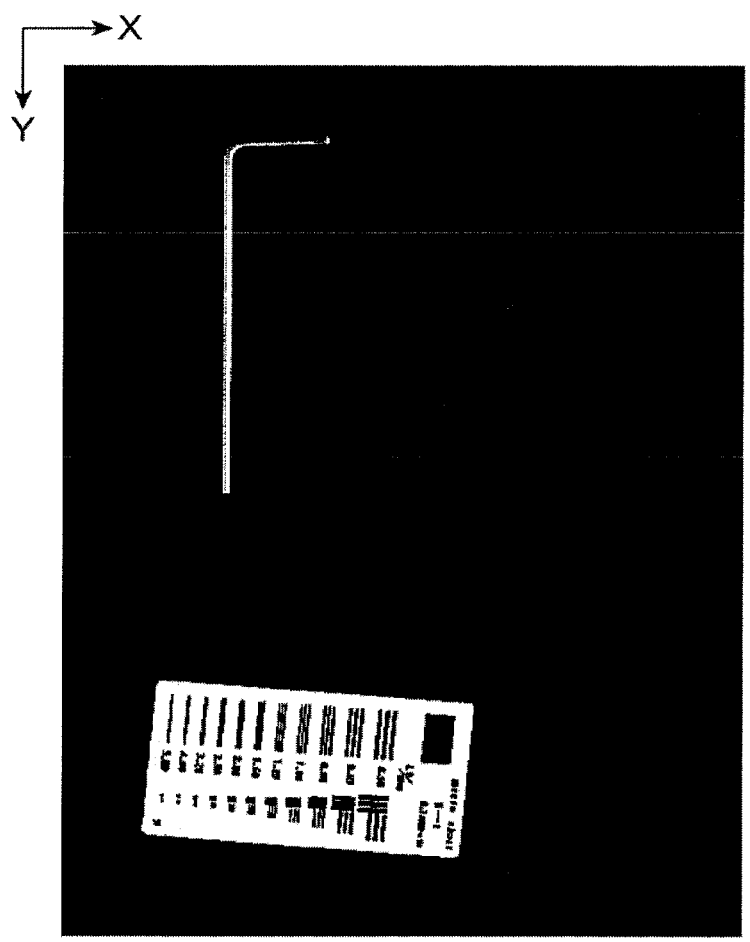
FIG. 11 shows a subtraction image based on the images shown in FIG. 10.

FIG. 9 is a view showing an image (a) detected by the low energy detector 32 and an image (b) detected by the high energy detector 42 when the detection timing control and the image correction processing according to the present embodiment are not carried out, and FIG. 10 is a view showing an image (a) detected by the low energy detector 32 and an image (b) detected by the high energy detector 42 when the detection timing control and the image correction processing according to the present embodiment are carried out. FIG. 11 shows a subtraction image based on the images shown in FIG. 10.

As shown in FIG. 9, the number of pixels in the conveying direction Y of the image from the low energy detector 32 and the number of pixels in the conveying direction Y of the image from the high energy detector 42 are different from each other, so that it is difficult to generate a subtraction image based on these images.

As shown in FIG. 10, by making the number of pixels in the conveying direction Y of the image from the low energy detector 32 and the number of pixels in the conveying direction Y of the image from the high energy detector 42 equal to each other, as shown in FIG. 11, a subtraction image in which only a desired substance is made to stand out can be easily obtained.

The present invention is not limited to the above-described embodiment, but various modifications are possible.

The present embodiment shows an example in which the timing control section 50, the low energy image correction section 34, and the high energy image correction section 44 are configured by hardware, however, the timing control section 50, the low energy image correction section 34, and the high energy image correction section 44 may be realized by, for example, software processing on an external computer. Specifically, it is possible that the timing control section and the image correction section according to the present invention are realized by computer programs, and the detection timing control processing and the pixel correction processing according to the present invention are carried out by software.

In the present embodiment, a case where the low energy detector 32 and the high energy detector 42 are arranged so that their left ends match each other is illustrated, however, various arrangements of the low energy detector 32 and the high energy detector 42 are possible. For example, the low energy detector 32 and the high energy detector 42 may be arranged so that their central axes match each other.

Thus, various arrangements of the low energy detector 32 and the high energy detector 42 are possible, however, depending on the arrangement, it is preferable that either the detection timings of the low energy detector 32 or the detection timings of the high energy detector 42 are delayed.

FIG. 12 is a diagram showing brightness files of images when detecting the same specimen. The specimen has a high-transmittance portion with a length corresponding to three pixels, and in FIG. 12(*a*), detection timings are adjusted so that the high-transmittance portion of the specimen can be detected at the detection timings 4 to 7. On the other hand, FIG. 12(*b*) shows a brightness file when the detection timings are different by a ½ pixel from the detection timings in FIG. 12(*a*), and FIG. 12(*c*) shows a brightness file when the detection timings are different by a ¼ pixel from the detection timings in FIG. 12(*a*).

Figure 13:
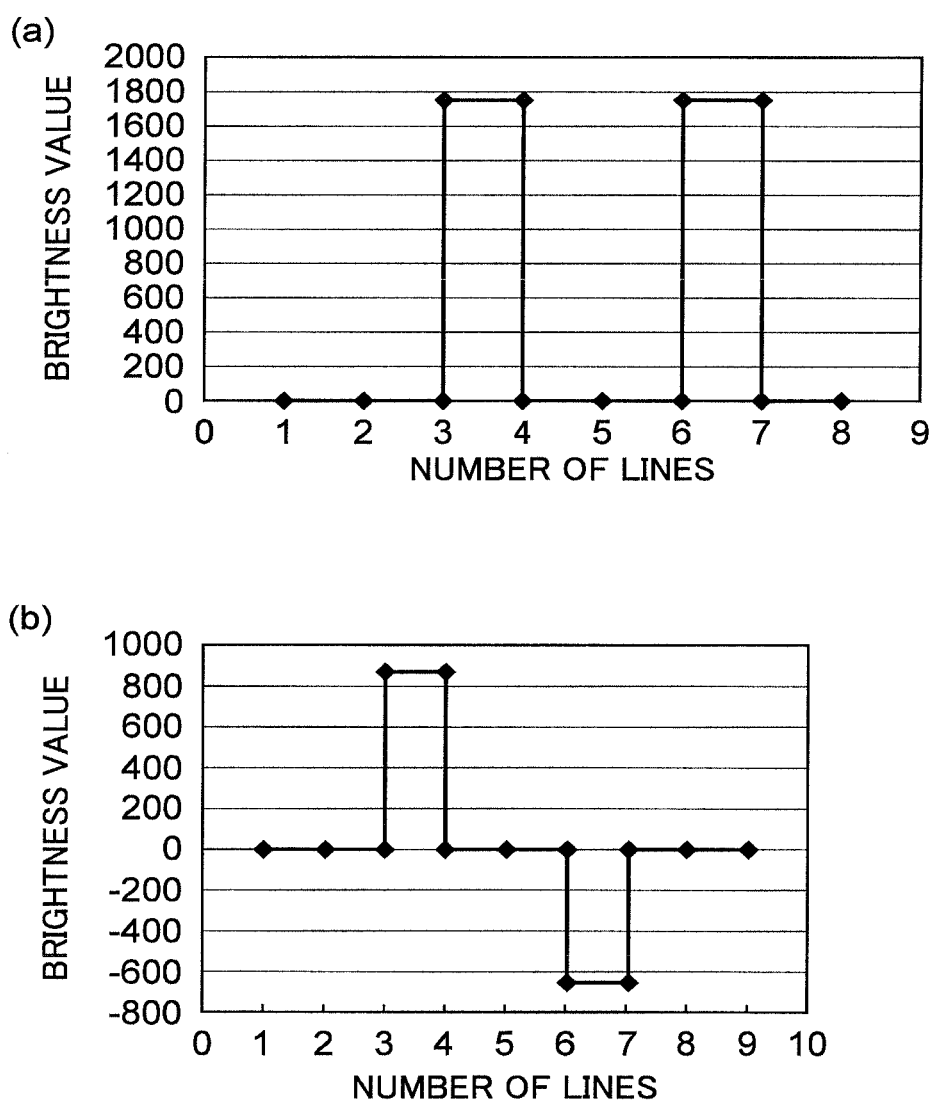
FIG. 13 is a diagram showing brightness files of subtraction images based on images with the brightness files shown in FIG. 12.

FIG. 13 is a diagram showing brightness files of subtraction images based on images with the brightness files shown in FIG. 12. FIG. 13(*a*) shows a brightness file of a subtraction image based on an image with the brightness file shown in FIG. 12(*a*) and an image with the brightness file shown in FIG. 12(*b*), that is, a brightness file of a subtraction image based on images the detection timings of which are different by a ½ pixel from each other. In FIG. 13(*a*), positive pseudo edges are generated before and after the high-transmittance portion of the specimen. This generation of positive pseudo edges becomes a cause of generation of white edges described later in a subtraction image. On the other hand, FIG. 13(*b*) shows a brightness file of a subtraction image based on an image with the brightness file shown in FIG. 12(*a*) and an image with the brightness file shown in FIG. 12(*c*), that is, a brightness file of a subtraction image based on images the detection timings of which are different by a ¼ pixel from each other. Referring to FIG. 13(*b*), a positive pseudo edge is generated before the high-transmittance portion of the specimen, and a negative pseudo edge is generated after the high-transmittance portion of the specimen. Generation of the positive pseudo edge becomes a cause of generation of a white edge described later in a subtraction image, and generation of a negative pseudo edge becomes a cause of generation of a black edge described later in a subtraction image.

Figure 14:
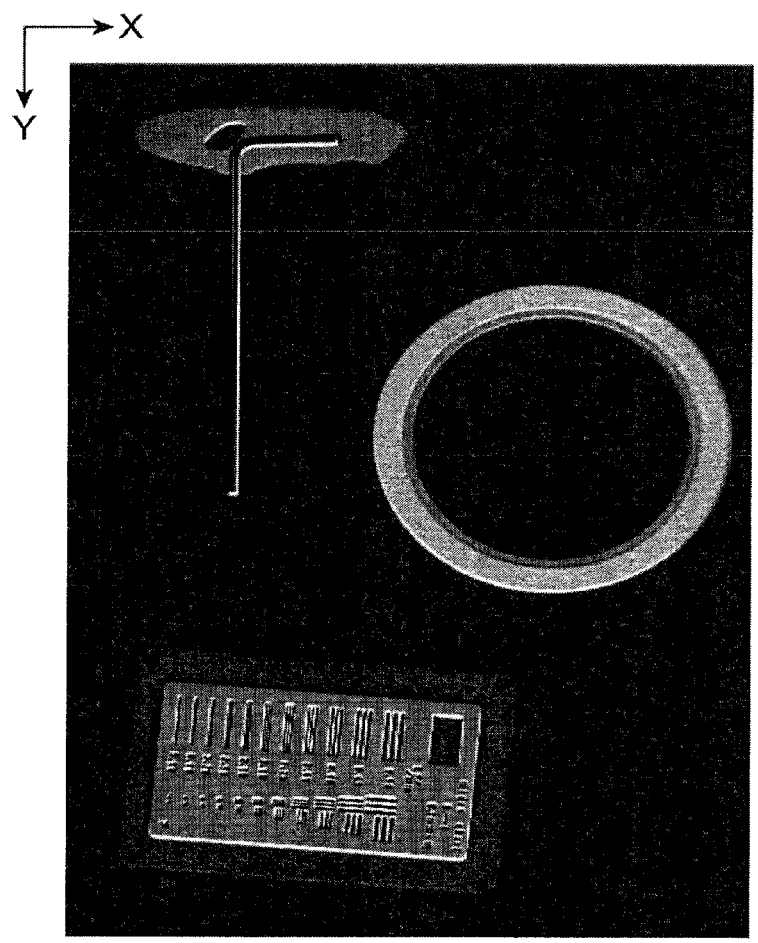
FIG. 14 is a diagram showing an example of a subtraction image based on two images the detection timings of which are different from each other.

FIG. 14 is a view showing an example of a subtraction image based on two images the detection timings of which are different from each other. Referring to FIG. 14, white edges are generated at portions on the lower sides of the substances in the specimen, and black edges are generated at portions on the upper sides. Thus, if the detection timings in two detectors for a detecting portion on a specimen differ greatly, an excellent subtraction image may not be obtained.

In this case, either the detection timings of the low energy detector 32 or the detection timings of the high energy detector 42 are preferably delayed so as to reduce the position deviations between the detection positions on the specimen at the detection timings of one detector and the detection positions on the specimen at the detection timings of the other detector. For example, as shown in FIG. 6, a delay time is applied to the detection timings of either one detector so that the low energy detector 32 detects only pixel data C not including adjacent pixel data B and D when detecting the third line, and the high energy detector 42 detects only pixel data B+C not including adjacent pixel data A and D when detecting the third line.

According to the study made by the inventors of the present invention, as long as the position deviations between the detection positions on a specimen at the detection timings of one detector and the detection positions on the specimen at the detection timings of the other detector were not more than 0.3 times the pixel width Wb1 of the pixel 326 in the low energy detector 32, generation of white edges and black edges could be reduced in the subtraction image. In other words, as long as the position deviations between the detection positions on a specimen at the detection timings of one detector and the detection positions on the specimen at the detection timings of the other detector were more than 0.3 times the pixel width Wb1 of the pixel 326 in the low energy detector 32, as described above, the delay time of either the detection timings of the low energy detector 32 or the detection timings of the high energy detector 42 must be adjusted so as to reduce the position deviations between the detection positions on the specimen at the detection timings of one detector and the detection positions on the specimen at the detection timings of the other detector.

In the present embodiment, in order to make the area S1 of each of the pixels 326 in the line sensor 324 of the low energy detector 32 smaller than the area S2 of each of the pixels 426 in the line sensor 424 of the high energy detector 42, the pixel width Wb1 of each pixel 326 is made smaller than the pixel width Wb2 of each pixel 426, however, it is also possible that, as shown in FIG. 15, the pixel width Wa1 of each pixel 326 may be made smaller than the pixel width Wa1 of each pixel 426. Thus, when the numbers of pixels in the detection direction X are different from each other, in order to make the numbers of pixels equal to each other, image thinning-out processing may be carried out in one radiation detector and image interpolation processing may be carried out in the other radiation detector.

INDUSTRIAL APPLICABILITY

The present invention is applicable to uses that make easy arithmetic processing based on radiation images acquired with two radiation detectors even when the numbers of pixels of the radiation detectors are different from each other.

REFERENCE SIGNS LIST

1 X-ray foreign substance inspection device
10 Belt conveyor
12 Belt portion
14 Belt conveyor control section
20 X-ray irradiator
30 Low energy image acquisition section
32 Low energy detector (first radiation detector)
322 Low energy scintillator layer (first scintillator layer)
324 Low energy line sensor (first pixel section)
326 Pixel
34 Low energy image correction section (first image processing section)
34a Amplifier
34b A/D converter
34c Correction circuit
34d Output interface
40 High energy image acquisition section
42 High energy detector (second radiation detector)
422 High energy scintillator layer (second scintillator layer)
424 High energy line sensor (second pixel section)
426 Pixel
44 High energy image correction section
44a Amplifier
44b A/D converter
44c Correction circuit
44d Output interface
50 Timing control section
60 Timing calculation section
70 Image processing device
80 Radiation detection device
86 Dual-energy sensor

The invention claimed is:

1. A radiation detection device for a foreign substance inspection using a subtraction method, which detects radiation in a first energy range and radiation in a second energy range higher than the radiation in the first energy range that are transmitted through a specimen and incident from a radiation incident direction, comprising:
a first radiation detector that is positioned on the upstream side with respect to the radiation incident direction, and detects radiation in the first energy range and generates an image corresponding to an image of the radiation;
a second radiation detector that is positioned on the downstream side with respect to the radiation incident direction, and detects radiation in the second energy range and generates an image corresponding to an image of the radiation;
a timing control section that controls detection timings of the first radiation detector and detection timings of the second radiation detector; and
an image correction section that corrects an image from the first radiation detector, wherein
the first radiation detector includes a first pixel section that has a plurality of pixels arrayed along an image detection direction and acquires a first image based on an image of radiation in the first energy range,
the second radiation detector includes a second pixel section that has a plurality of pixels arrayed along the image detection direction and acquires a second image based on an image of radiation in the second energy range,
a first pixel width Wb1 in an orthogonal direction orthogonal to the image detection direction of each of the plurality of pixels in the first pixel section is smaller than a second pixel width Wb2 in the orthogonal direction of each of the plurality of pixels in the second pixel section,
the timing control section synchronizes detection timings of the second radiation detector to detection timings of the first radiation detector, and
the image correction section sums Wb2/Wb1 pixel data successive in the image from the first radiation detector based on a ratio Wb2/Wb1 of the second pixel width Wb2 to the first pixel width Wb1.

2. The radiation detection device according to claim 1, wherein
the first radiation detector and the second radiation detector are arranged so that position deviations between detection positions on a specimen at detection timings of the first radiation detector and detection positions on the specimen at detection timings of the second radiation detector are not more than 0.3 times the first pixel width.

3. The radiation detection device according to claim 1, wherein
the timing control section delays either the detection timings of the first radiation detector or the detection timings of the second radiation detector.

4. The radiation detection device according to claim 1, wherein
the first radiation detector includes a first scintillator layer that extends along the image detection direction and converts an image of radiation in the first energy range into an optical image, and the first pixel section that acquires the first image based on the optical image converted by the first scintillator layer, and the second radiation detector described above includes a second scintillator layer that extends along the image detection direction and converts an image of radiation in the second energy range into an optical image, and the second pixel section that acquires the second image based on the optical image converted by the second scintillator layer.

* * * * *